United States Patent [19]

Mandeville, III et al.

[11] Patent Number: 5,900,475
[45] Date of Patent: May 4, 1999

[54] HYDROPHOBIC SEQUESTRANT FOR CHOLESTEROL DEPLETION

[75] Inventors: W. Harry Mandeville, III, Lynnfield; Stephen Randall Holmes-Farley, Arlington; John S. Petersen, Acton, all of Mass.

[73] Assignee: GelTex Pharmaceuticals, Inc., Waltham, Mass.

[21] Appl. No.: 08/659,264

[22] Filed: Jun. 6, 1996

Related U.S. Application Data

[63] Continuation-in-part of application No. 08/469,659, Jun. 6, 1995, Pat. No. 5,618,530, which is a continuation-in-part of application No. 08/258,431, Jun. 10, 1994, abandoned, and application No. 08/332,096, Oct. 31, 1994, abandoned.

[51] Int. Cl.[6] .................................................. C08G 79/02
[52] U.S. Cl. .......................... 528/392; 528/272; 528/288; 528/299; 528/302; 528/303; 528/397; 525/437; 525/445; 552/548
[58] Field of Search .................................... 528/272, 288, 528/299, 302, 303, 392, 397; 525/437, 445, 382.2; 522/1; 514/772.3; 552/548; 524/547, 551, 555, 815

[56] References Cited

U.S. PATENT DOCUMENTS

| | | | |
|---|---|---|---|
| 2,874,132 | 2/1959 | Riener | 524/815 |
| 3,288,770 | 11/1966 | Butler | 260/88.3 |
| 3,308,020 | 3/1967 | Wolf et al. | 167/65 |
| 3,383,281 | 5/1968 | Wolf et al. | 167/65 |
| 3,562,266 | 2/1971 | Minisci et al. | 528/176 |
| 3,692,895 | 9/1972 | Nelson et al. | 424/78 |
| 3,780,171 | 12/1973 | Irmscher et al. | 424/79 |
| 3,787,474 | 1/1974 | Daniels et al. | 260/459 |
| 3,801,641 | 4/1974 | Payot et al. | 528/176 |
| 3,803,237 | 4/1974 | Lednicer et al. | 528/176 |
| 3,980,770 | 9/1976 | Ingelman et al. | 424/79 |
| 4,027,009 | 5/1977 | Grier et al. | 424/78 |
| 4,071,478 | 1/1978 | Shen et al. | 260/2 R |
| 4,098,726 | 7/1978 | Wagner et al. | 528/403 |
| 4,101,461 | 7/1978 | Strop et al. | 521/32 |
| 4,111,859 | 9/1978 | Strop et al. | 521/33 |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |
| 4,426,489 | 1/1984 | Wessling et al. | 524/815 |
| 4,540,760 | 9/1985 | Harada et al. | 526/211 |
| 4,557,930 | 12/1985 | Kihara et al. | 424/79 |
| 4,559,391 | 12/1985 | Ueda et al. | 525/366 |
| 4,605,701 | 8/1986 | Harada et al. | 525/107 |
| 4,680,360 | 7/1987 | Ueda et al. | 526/310 |
| 4,759,923 | 7/1988 | Buntin et al. | 424/440 |
| 5,055,197 | 10/1991 | Albright et al. | 210/638 |
| 5,236,701 | 8/1993 | St. Pierre et al. | 424/78 |
| 5,374,422 | 12/1994 | St. Pierre et al. | 424/78.12 |
| 5,414,068 | 5/1995 | Bliem et al. | 528/288 |
| 5,430,110 | 7/1995 | Ahlers et al. | 525/328.2 |
| 5,451,397 | 9/1995 | Albright et al. | 424/78.01 |
| 5,462,730 | 10/1995 | McTaggart et al. | 424/78.35 |

FOREIGN PATENT DOCUMENTS

| | | |
|---|---|---|
| 0 081 291 A3 | 6/1983 | European Pat. Off. . |
| 0 162 388 | 11/1985 | European Pat. Off. . |
| 0 323 847 A1 | 7/1989 | European Pat. Off. . |
| 0 373 852 A2 | 6/1990 | European Pat. Off. . |
| 0432995A1 | 6/1991 | European Pat. Off. . |
| 0 459 632 A1 | 12/1991 | European Pat. Off. . |
| 0 580 079 A1 | 1/1994 | European Pat. Off. . |
| 798488 | 7/1958 | United Kingdom . |
| 929391 | 6/1963 | United Kingdom . |
| 1567294 | 5/1980 | United Kingdom . |
| WO91/18027 | 11/1991 | WIPO . |
| WO92/10522 | 6/1992 | WIPO . |
| WO94/04596 | 3/1994 | WIPO . |
| WO94/27620 | 8/1994 | WIPO . |
| WO 95/34588 | 12/1995 | WIPO . |

OTHER PUBLICATIONS

Heming, A.E. and Flanagan, Thomas L., "Considerations in the Selection of Cation Exchange Resins for Theraoeutic Use," *Annals of the New York Academy of Sciences*, 57:239–251 (1954).

McCarthy, Peter A., "New Approaches to Atherosclerosis: An Overview," *Medicinal Research Review*, 13(2):139–159 (1993).

*Primary Examiner*—Terressa Mosley
*Attorney, Agent, or Firm*—Hamilton, Brook, Smith & Reynolds, P.C.

[57] ABSTRACT

The present invention relates to a poly(allylamine) polymer and, more generally, a hydrocarbon amine polymer. Preferably, these polymers are crosslinked. The present invention also relates to methods of forming these polymers and methods for their use. Further, the present invention relates to alkylating agents that can be employed to form the polymers and to methods for forming the alkylating agents. Generally, the polymer sequestrant includes a substituent bound to an amine of the polymer. The substituent includes a quaternary amine-containing moiety having one, two or three terminal hydrophobic substituents. A method of preparing quaternary amine-containing alkylating agents includes reacting an unsymmetrical dihalide with a tertiary amine having at least one hydrophobic substituent. A method for binding bile salts of bile acids in a mammal includes orally administering to the mammal a therapeutically-effective amount of the polymer sequestrant.

54 Claims, No Drawings

HYDROPHOBIC SEQUESTRANT FOR CHOLESTEROL DEPLETION

RELATED APPLICATIONS

This is a Continuation-in-Part of application Ser. No. 08/469,659, filed Jun. 6, 1995, now U.S. Pat. No. 5,618,530, which is a Continuation-in-Part of application Ser. No. 08/258,431, filed Jun. 10, 1994, now abandoned, and of application Ser. No. 08/332,096, filed Oct. 31, 1994, now abandoned, the teachings of all of which are incorporated herein in their entirety

BACKGROUND OF THE INVENTION

Salts of bile acids act as detergents to solubilize and consequently aid in digestion of dietary fats. Bile acids are derived from cholesterol and consequently, removing bile acids can result in reduction in cholesterol Following digestion, bile acids can be passively absorbed in the jejunum, or reabsorbed by active transport in the ileum Bile acids which are not reabsorbed are lost.

Reabsorption of bile acids from the intestine conserves lipoprotein cholesterol in the bloodstream Conversely, blood cholesterol level can be diminished by reducing reabsorption of bile acids.

One method of reducing the amount of bile acids that are reabsorbed is oral administration of compounds that sequester the bile acids and cannot themselves be absorbed The sequestered bile acids are consequently excreted Many bile acid sequestrants, however, do not bind conjugated primary bile acids, such as conjugated cholic acid well enough to prevent substantial portions from being reabsorbed. In addition, the volume of sequestrants that can be ingested is limited. As a result, the effectiveness of many sequestrants to diminish blood cholesterol levels is also limited.

Further, the synthesis of many sequestrants can be limited by the expense and reaction yield associated with preparing-suitable precursors. For example, alkylating agents employed to modify polymers can be difficult to prepare. In addition, the ability of an alkylating agent to react with a polymer can also limit the effectiveness of the resulting sequestrant.

A need exists, therefore, for a sequestrant and a method which overcomes or minimizes the referenced problems.

SUMMARY OF THE INVENTION

The present invention relates to a poly(allylamine) polymer and, more generally, a hydrocarbon amine polymer. Preferably, these polymers are crosslinked. The present invention also relates to methods of forming these polymers and methods for their use. Further, the present invention relates to alkylating agents that can be employed to form the polymers and to methods for forming the alkylating agents.

In one embodiment, the poly(allylamine) polymer is crosslinked and comprises a substituent bound to an amine of the polymer. The substituent includes a quaternary amine-containing moiety, wherein a quaternary amine nitrogen of the moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently alkyl groups having from one to about five carbons.

The method for forming the crosslinked poly(allylamine) polymers includes reacting a crosslinked poly(allylamine) with a quaternary amine-containing compound having the formula

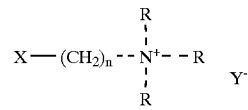

wherein,

R represents an alkyl group, at least one of which has from six to about twenty-four carbons and the remainder of which each independently have from one to about five carbons, n is an integer having a value of three or more, X is a leaving group, and Y is a negatively-charged counterion.

In another embodiment, the present invention relates to a hydrocarbon amine polymer that includes a substituent bound to an amine of the polymer. The substituent includes a quaternary amine-containing moiety, wherein a quaternary amine nitrogen of said moiety is bound to the amine of the polymer by an alkylene having three or more carbons and wherein at least two of three terminal substituents of the quaternary amine are each a hydrophobic alkyl group having from six to about twenty-four carbons and the other terminal substituent is an alkyl group having from one to about five carbons.

The method of forming a crosslinked hydrocarbon amine polymer of the invention includes the step of reacting a crosslinked hydrocarbon amine polymer with a quaternary ammonium compound having the formula

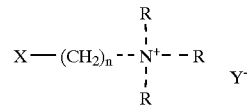

wherein,

R represents an alkyl groups at least one of which has from six to about twenty-four carbons and the remainder of which each independently have from one to about five carbons, n is an integer having a value of three or more, X is a leaving groups and Y is a negatively-charged counterion.

Methods of use of the poly(allylamine) polymer and hydrocarbon amine polymers of the invention include their oral administration to a mammal in a therapeutic amount to bind bile salts, reduce blood cholesterol, treat atherosclerosis, treat hypercholesterolemia or reduce plasma lipid content of the mammal.

In another embodiment, the invention is a quaternary ammonium compound having the formula

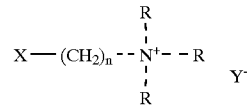

wherein,

R represents an alkyl group, at least one of which has from six to about twenty-four carbons and the remainder of which each independently have from one to about five carbons, n is an integer having a value of three or more, X is a leaving group, and Y is a negatively-charged counterion.

A method of forming a quaternary ammonium compound includes the step of reacting a tertiary amine, having the formula

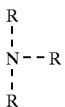

wherein,

R represents an alkyl group, at least one of which has from six to about twenty-four carbons and the remainder of which each independently have from one to about five carbons, with an unsymmetrical dihalide having the formula $$X^1-(CH_2)_n-X^2$$

wherein $X^1$ is chloride, $X^2$ is bromide, and n is an integer with a value of 3 or greater.

This invention has many advantages. For example, the poly(allylamine) and hydrocarbon amine polymer sequestrants of the invention bind conjugated bile acids, including primary bile acids, that would otherwise be reabsorbed by active transport One possible explanation for the improved performance of the polymer sequestrants of the invention in binding bile acids could be their ability to form both hydrogen and ionic bonds with bile acids. Hydrogen bonds can be formed by the secondary amine component of the polymer, while ionic bonds can be formed by the quaternary amine substituent. Further, the external, or terminal, distribution of hydrophobic components of the polymer sequestrants relative to the backbone of the polymer and relative to the secondary and quaternary amine components of the polymer can contribute to significantly increasing the effectiveness of each given dosage of sequestrant. In addition, the presence of two or more hydrophobic alkyl groups as terminal substituents ha the advantage of providing more sites for hydrophobic binding of the bile salts.

The method of forming the polymer sequestrant of the invention also includes several advantages For example, alkylation of an amine component of a hydrocarbon amine polymer, such as a poly(allylamine) polymer, with a quaternary amine can be facilitated by employing a quaternary amine that will be reactive with the amine component at a leaving group bearing-carbon atom that is at least three carbon atoms removed from the quaternary ammonium center. In addition, it is believed that performance of the resulting sequestrant can be improved as a consequence of employing an alkylene group of at least three carbons to bind the quaternary amine to an amine of a hydrocarbon amine polymer, and particularly to a poly-(allylamine) polymer.

Use of unsymmetrical dihalides in preparation of the quaternary amine-containing alkylating agents of the present invention can result in an increased yield and purity of desired product. Since the halogens in an unsymmetrical dihalide are not equivalent in reactivity, the carbon bearing the more reactive halogen will react almost exclusively, thereby forming a relatively pure compound in a good yield. This relatively pure quaternary amine-containing alkylating agent can then be used to alkylate an amine nitrogen of the hydrocarbon amine polymer backbone.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A "hydrocarbon amine polymer," as that termed is employed herein, means a polymer consisting essentially of carbon, hydrogen and nitrogen. Preferably, the hydrocarbon amine polymer is crosslinked. More preferably, the hydrocarbon amine polymer is a poly(allylamine) polymer. Most preferably, the hydrocarbon amine polymer is a crosslinked poly(allylamine) polymer. Other examples of suitable hydrocarbon amine polymers include poly(vinylamine) and poly(ethyleneimine) polymers.

The hydrocarbon amine polymer sequestrant of the invention includes a substituent bound to an amine of the polymer. The substituent includes a quaternary amine moiety, wherein the quaternary amine nitrogen of said moiety is bound to the amine of the polymer backbone by an alkylene having three or more carbons. At least one of the three terminal substituents of the quaternary amine is a hydrophobic alkyl group having from six to about twenty-four carbons. The remaining terminal substituents are each independently alkyl groups having from one to about five carbons.

A "terminal substituent" of the quaternary amine, as the term is employed herein, is any one of the three substituents on the quaternary amine nitrogen which is not the carbon chain between the amine on the polymer backbone and the amine of the quaternary ammonium center.

A "hydrophobic alkyl group," as that term is employed herein, is an alkyl group having from six to about twenty-four carbons and which is terminated in a hydrophobic moiety. The hydrophobic alkyl group can be, for example, an aliphatic, aromatic, branches, or cyclic carbon chain. The hydrophobic substituent does not include the alkylene between the nitrogen of the amine polymer backbone and the nitrogen of the quaternary ammonium center.

In one embodiment, the hydrocarbon amine polymer is a crosslinked poly(allylamine) polymer and comprises a substituent bound to an amine of the polymer. The substituent includes a quaternary amine-containing moiety, wherein a quaternary amine nitrogen of the moiety is bound to the amine of the polymer by an alkylene having three or more carbons and wherein at least one of three terminal substituents of the quaternary amine is a hydrophobic alkyl group having from six to about twenty-four carbons. The remaining terminal substituents are each independently alkyl groups having from one to about five carbons.

Preferred embodiments include a crosslinked poly (allylamine) polymer wherein the alkylene is three carbons in length, at least one of the three terminal substituents of the quaternary amine is a hydrophobic alkyl group which is either an octyl, decyl or dodecyl group and the remaining terminal substituents are methyl groups Other preferred embodiments include a crosslinked poly (allylamine) polymer wherein the alkylene is four carbons in length, at least one of the three terminal substituents of the quaternary amine is a hydrophobic alkyl group which is either an octyl, decyl or dodecyl group and the remaining terminal substituents are methyl groups.

Another preferred embodiments include a crosslinked poly(allylamine) polymer wherein the alkylene is five carbons in length, at least one of the three terminal substituents of the quaternary amine is a hydrophobic alkyl group which is either an octyl, decyl or dodecyl group and the remaining terminal substituents are methyl groups Still other preferred embodiments include a crosslinked poly(allylamine) polymer wherein the alkylene is six carbons in length, at least one of the three terminal substituents of the quaternary amine is a hydrophobic alkyl group which is either an octyl, decyl or dodecyl group and the remaining terminal substituents are methyl groups.

In one embodiment, poly(allylamine) polymer of the invention has the following general formula

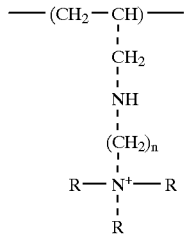

wherein, n has a value of three or more, and

R represents an alkyl group, at least one of which has from six to about twenty-four carbons and the remainder of which each independently have from one to about five carbons.

The method for forming the crosslinked poly(allylamine) polymers includes reacting a crosslinked poly(allylamine) with a quaternary amine-containing compound having the formula

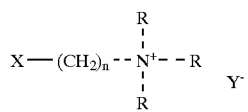

wherein,

R represents an alkyl group, at least one of which has from six to about twenty-four carbons and the remainder of which each independently have from one to about five carbons, n is an integer having a value of three or more, X is a leaving group, and Y is a negatively-charged counterion.

Preferred embodiments of the crosslinked poly (allylamine) formed by this method include a crosslinked poly(allylamine) polymer wherein the alkylene is three carbons in length, at least one of the three terminal substituents of the guaternary amine is a hydrophobic alkyl group which is either an octyl, decyl or dodecyl group and the remaining terminal substituents are methyl groups.

Other preferred embodiments of the crosslinked poly (allylamine) prepared by this method include a crosslinked poly(allylamine) polymer wherein the alkylene is four carbons in length, at least one of the three terminal substituents of the quaternary amine is a hydrophobic alkyl group which is either an octyl, decyl or dodecyl group and the remaining terminal substituents are methyl groups.

Additional preferred embodiments of the crosslinked poly (allylamine) formed by this method include a crosslinked poly(allylamine) polymer wherein the alkylene is five carbons in length, at least one of the three terminal substituents of the quaternary amine is a hydrophobic alkyl group which is either an octyl, decyl or dodecyl group and the remaining terminal substituents are methyl groups.

Still other preferred embodiments of a crosslinked poly (allylamine) formed by this method, include a crosslinked poly(allylamine) polymer wherein the alkylene is six carbons in length, at least one of the three terminal substituents of the quaternary amine is a hydrophobic alkyl group which is either an octyl, decyl or dodecyl group and the remaining terminal substituents are methyl groups.

In another embodiment, the present invention relates to a hydrocarbon amine polymer that includes a substituent bound to an amine of the polymer. The substituent includes a quaternary amine-containing moiety, wherein a quaternary amine nitrogen of said moiety is bound to the amine of the polymer by an alkylene having three or more carbons and wherein at least two or all three of the terminal substituents of the quaternary amine are each a hydrophobic alkyl group having from six to about twenty-four carbons. In the case where two of three terminal substituents of the quaternary amine are each a hydrophobic alkyl group, the other terminal substituent is an alkyl group having from one to about five carbons. In a preferred embodiment, the hydrocarbon amine polymer is crosslinked The method of forming a crosslinked hydrocarbon amine polymer of the invention includes the step of reacting a crosslinked hydrocarbon amine polymer with a quaternary ammonium compound having the formula

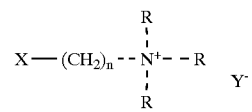

wherein,

R represents an alkyl group, at least one of which has from six to about twenty-four carbons and the remainder of which each independently have from one to about five carbons, n is an integer having a value of three or more, X is a leaving group, and Y is a negatively-charged counterion.

Preferred embodiments of the crosslinked hydrocarbon amine polymer formed by this method include, poly (vinylamine), poly(allylamine) and poly(ethyleneimine) polymers.

Methods of use of the poly(allylamine) polymers and hydrocarbons amine polymers of the invention include their oral administration to a mammal in a therapeutic amount to bind bile salts, reduce blood cholesterol, treat atherosclerosis, treat hypercholesterolemia or reduce plasma lipid content of the mammal. Generally, a therapeutic amount of the hydrocarbon amine polymers or poly (allylamine) polymers, is an amount in a range of from about 0.1 grams/day to about twenty grams/day.

In one embodiment, the method of the invention is a method for binding bile salts in a mammal, comprising the step of orally administering to the mammal a therapeutic amount of the hydrocarbon amine polymer of the invention In another embodiment, the method of the invention is a method for binding bile salts in a mammal, comprising the step of orally administering to the mammal a therapeutic amount of the poly(allylamine) polymer of the present invention.

In another embodiment, the invention is a method for reducing blood cholesterol in a mammal, comprising the step of administering to the mammal a therapeutic amount of the hydrocarbon amine polymer, preferably a crosslinked poly(allylamine) polymer, of the invention. In still another embodiment, the invention includes a method for treating atherosclerosis in a mammal, comprising the step of administering to the mammal a therapeutic amount of the hydrocarbon amine polymer, preferably a crosslinked poly (allylamine) polymer, of the invention. In still another embodiment, the method of the invention is that of treating hypercholesterolemia in a mammal, comprising the step of administering to the mammal a therapeutic amount of the hydrocarbon amine polymer, preferably a crosslinked poly (allylamine) polymer of the inventions.

Another embodiment of the invention is a method for reducing plasma lipid content of a mammal, comprising the step of orally administering to the mammal a polymer of the invention to tightly sequester conjugated bile acids secreted by the mammal, whereby a substantial portion of the conjugated bile acids are excreted by the mammal, thereby causing accelerated lipid metabolization and consequent lowering of plasma lipid content of the mammal. In a preferred embodiment, the sequestered conjugated primary bile acids include conjugated primary bile acids, such as conjugated cholic acid and conjugated chenodeoxycholic acid.

The hydrocarbon amine polymers and poly(allylamine) polymers of this invention are particularly suitable for binding conjugated primary bile acids, such as glycocholic and glycochenodeoxycholic acids, in mammals by oral administration of the polymer. A particularly suitable form for oral administration of the hydrocarbon amine polymer and poly(allylamine) polymer is that which will form a gel in the stomach of a patient.

Examples of suitable methods by which the preferred amine polymer of the invention can be formed are shown below:

1. One method involves polymerization of an amine monomer to form a homopolymer. Examples of this method include polymerization of allylamine, ethyleneimine, vinylamine, 1,2-diaminoethene, aminopropylacrylate, or p-aminomethylstyrene, to form their respective homopolymers.
2. Another method involves copolymerizing an amine monomer with one or more additional monomers. These additional monomers include amine monomers, such as those listed above, and non-amine monomers, such as acrylamide, styrene, divinylbenzene, vinyl alcohol, or vinyl chloride. Examples include copoly (allylamine/acrylamide), copoly(vinylamine/allylamine), and copoly(allylamine/divinylbenzene).
3. Still another method involves polymerization of a non-amine monomer to form a homopolymer that is subsequently chemically modified to form an amine polymer. Examples of this method include polymerization of vinyl formamide, vinyl acetamide, vinyl chloride, vinyl bromide, allyl chloride, allyl bromide, acrylamide, or acrylonitrile, to form their respective homopolymers. Each homopolymer would then be chemically altered to form an amine polymer using such reactions as hydrolysis, nucleophilic substitution, or reduction. The first four homopolymers listed above would then become poly (vinylamine) and the last four would become poly (allylamine). It is to be understood that not all of the initial non-amine monomer need be chemically altered, resulting in an amine polymer that contains some of the initial non-amine monomers in a non-amine state.
4. A fourth method involves copolymerizing a non-amine monomer with one or more additional monomers. These additional monomers could include amine monomers, such as those listed in the first method, and non-amine monomers, such as those listed in the third method. The resulting copolymer would then be chemically altered to form an amine polymer as in the third method. Examples would include copolymerization of acrylamide and styrene, followed by reduction to form copoly(allylamine/styrene), copolymerization of acrylonitrile and vinyl formamide, followed by reduction and hydrolysis, to form copoly (allylamine/vinylamine), and copolymerization of acrylonitrile and allylamine, followed by reduction, to form poly (allylamine). It is to be understood that not all of the initial non-amine monomer be chemically altered, resulting in an amine polymer that contains some of the initial non-amine monomers in a non-amine state.
5. A fifth method involves forming an amine polymer through a condensation mechanism. Examples of this method would include reaction of diethylenetriamine and epichlorohydrin, 1,3-dibromopropane and ethylenediamine, spermine and 1,4-butanediol diglycidyl ether, or tris(2-aminoethyl)amine and 1,10-dibromodecane.

Each of these amine polymers typically has a molecular weight greater than about 2,000. Examples of resulting suitable hydrocarbon amine polymers include poly (vinylamine), poly(allylamine), and poly(ethyleneimine) polymers. A preferred hydrocarbon amine polymer is poly (allylamine) polymers.

Preferably, the hydrocarbon amine polymer is crosslinked, such as by reacting the polymer with a suitable crosslinking agent. Examples of suitable crosslinking agents include acryloyl chloride, epichlbrohydrin, butanedioldiglycidyl ether, ethanedioldiglycidyl ether, dimethyl succinate, etc. Epichlorohydrin is a preferred crosslinking agent. Typically, the amount of crosslinking agent that is reacted with the hydrocarbon amine polymer is sufficient to cause between about 0.5 and twenty percent of the sites available for reaction to react with the crosslinking agent. In one preferred embodiment, between about 0.5 and six percent of the amine groups of a hydrocarbon amine polymer react with the crosslinking agent. In another preferred embodiment, between about two and about twelve percent of the amine groups of a hydrocarbon amine polymer react with the crosslinking agent.

Crosslinking of the polymer can be achieved by reacting the polymer with a suitable crosslinking agent in an aqueous solution at about 25° C. for a period of time of about eighteen hours to thereby form a gel. The gel is then combined with water or dried to form a particulate solid. The particulate solid can then be washed with water and dried under suitable conditions, such as a temperature of about 50° C. for a period of time of about eighteen hours.

The hydrocarbon amine polymer can be alkylated to form the sequestrants of the invention. An "alkylating agent," as that term is employed herein, means a reactant that, when reacted with a hydrocarbon amine polymer, causes the nitrogen atom of a quaternary amine-containing moiety to be covalently bound to one or more of the backbone amines of the hydrocarbon amine polymer by a alkylene having three or more carbons. Suitable alkylating agents of the present invention can be quaternary ammonium compounds Therefore, in another embodiment, the invention is a quaternary ammonium compound having the formula

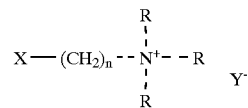

wherein,
R represents an alkyl group, at least one of which has from six to about twenty-four carbons and the remainder of which each independently have from one to about five carbons, n is an integer having a value of three or more, X is a leaving group, and Y is a negatively-charged counterion.

In one embodiment, X is a halide. Preferably, the value of n is in a range of from three to six. In other embodiments, one or two of said alkyl groups is a methyl group.

Particular examples of quaternary ammonium compounds suitable as alkylating agents include the following:
(4-bromobutyl)dioctylmethylammonium bromide;
(3-bromopropyl)dodecyldimethylammonium bromide;
(3-chloropropyl)dodecyldimethylammonium bromide;
(3-bromopropyl)octyldimethylammonium bromide;
(3-chloropropyl)octyldimethylammonium bromide;
(3-iodobutyl)dioctylmethylammonium bromide;
(2,3-epoxypropyl)decyldimethylammonium bromide;
(3-chloropropyl)decyldimethylammonium bromide;
(5-tosylpentyl)dodecyldimethylammonium bromide;
(6-bromohexyl)octyldimethylammonium bromide;
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-chloropropyl)hexyldimethylammonium bromide;
(3-chloropropyl)methyldioctylammonium bromide;
(3-chloropropyl)methyldidecylammonium bromide;
(3-chloropropyl)cyclohexyldimethylammonium bromide;
(3-chloropropyl)tetradecyldimethylammonium bromide; etc.

It is to be understood that the above compounds can be employed in halogenated forms including bromides, chlorides, and iodides as well as other negatively charged ions such as acetate, nitrate, sulfate, p-toluenesulfonate etc.

An example of a suitable method by which the preferred quaternary ammonium compounds, useful as alkylating agents of the invention, can be formed includes the includes the steps of reacting a tertiary amine, having the formula

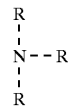

wherein,

R represents an alkyl group, at least one of which has from six to about twenty-four carbons, and the remainder of which each independently have from one to about five carbons, with an unsymmetrical dihalide having the formula

wherein $X^1$ is chloride, $X^2$ is bromide, and n is an integer with a value of 3 or greater.

In other embodiments the tertiary amine can have two or all three alkyl or substituted alkyl groups having from six to about twenty-four carbons. In the case of two, the remaining alkyl group has from one to about five carbons. Typically, alkylation is accomplished by combining the substituted tertiary amine with a suitable dihalide in an organic solvent. An example of a suitable symmetric dihalide is a dichloride. An example of a preferred dichloride is 1,3 dichloropropane.

Preferred dihalides of this invention also include unsymmetrical dihalides. "Unsymmetrical dihalides," as defined herein, are those dihalides wherein the halogens of the dihalide are not the same and consequently do not have the same reactivity as alkylating agents. Suitable examples of unsymmetrical dihalides include 1-bromo-3-chloropropane and 1-bromo-4-chlorobutane. Typically, when the dihalide is a bromide/chloride combination the bromide bearing end of the molecule is more reactive than the chloride bearing end of the molecule. Thus reaction of the unsymmetrical dihalide can result in almost exclusive reaction at the bromide bearing end leaving the chloride end unreacted. This relatively pure compound can then be used to alkylate the nitrogen of the hydrocarbon amine polymer, with reaction taking place at the chloride end. Use of the unsymmetrical dihalides increases both yield and purity of the resulting quaternary amine-containing alkylating agents, by avoiding undesirable side reactions which normally occur using symmetrical dihalides. Examples of suitable organic solvents include methanol, diethyl ether, etc. A preferred organic solvent is methanol.

The reaction is maintained at a temperature and for a period of time sufficient to allow reaction of the tertiary amine with the unsymmetrical dihalide. These parameters are typically dependent on the nature of the reactants and can be determined by one of ordinary skill in the art using no more than routine experimentation.

The reaction is terminated by removal of the solvent by suitable methods. The crude quaternary amine-containing alkylating agent is prepared for further reaction by methods known to those of ordinary skill in the art.

The hydrocarbon amine polymer is typically alkylated by combining the polymer with the quaternary amine-containing alkylating agent in an organic solvent or water. The amount of the alkylating agent combined with the hydrocarbon amine polymer is generally sufficient to cause reaction of the alkylating agent with greater than about five percent of the reactive nitrogens on the hydrocarbon amine polymer. Examples of suitable solvents include methanol, ethanol, acetonitrile, water, etc. Preferred solvents are water and methanol.

In a particularly preferred embodiment of the invention, the hydrocarbon amine polymer is a crosslinked poly (allylamine), wherein the substituent includes (3-propyl) dodecyldimethylammonium chloride. Alternatively, the hydrocarbon amine polymer is a crosslinked poly (allylamine), wherein the substituent includes butyldioctyl-methylammonium chloride. Further, the particularly preferred crosslinked poly(allylamine) is crosslinked by epichlorohydrin that is present in a range of from about one-half and about six percent of the amines of the polymer.

The hydrocarbon amine polymer of the invention can be subsequently treated or combined with other materials to form a composition for oral administration of the hydrocarbon amine polymer.

The present pharmaceutical compositions are generally prepared by known procedures using well known and readily available ingredients. In making the compositions of the present invention, the hydrocarbon amine polymer can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, and talc.

A negatively-charged counterion of the pharmaceutical composition can include organic ions, inorganic ions, or combinations thereof. Inorganic ions suitable for use in this invention include halide (especially chloride), carbonate and bicarbonate Suitable organic ions include acetate and benzoate.

The invention will now be further and specifically described by the following examples. All parts and percentages are by weight unless otherwise specified.

EXAMPLE 1

Preparation of Poly(allylamine) Hydrochloride Crosslinked with Epichlorohydrin

To a five gallon vessel was added poly(allylamine) hydrochloride (1 kg) obtained from Nitto Boseki and water (4 L). The mixture was stirred to dissolve the hydrochloride and the pH was adjusted by adding solid NaOH (284 grams) The resulting solution was cooled to room temperature, after which epichlorohydrin crosslinking agent (50 mL) was added all at once with stirring The resulting mixture was stirred gently until it gelled (about thirty-five minutes) The crosslinking reaction was allowed to proceed for an additional eighteen hours at room temperature, after which the polymer gel was removed and placed in portions in a blender with a total of 10 L of water. Each portion was blended gently for about three minutes to form coarse particles which were then stirred for one hour and collected by filtration. The solid was rinsed three times by suspending it in water (10 L, 15 L, 20 L) stirring each suspension for one hour, and collecting the solid each time by filtration. The resulting solid was then rinsed once by suspending it in isopropanol (17 L), stirring the mixture for one hour, and then collecting the solid by filtration, after which the solid was dried in a vacuum oven at 50° C. for eighteen hours to yield about 677 grams of the crosslinked polymer as a granular, brittle, white solid.

EXAMPLE 2

Alkylation of Crosslinked Poly(allylamine) with (3-bromopropyl)dodecyldimethylammonium bromide Crosslinked poly(allylamine) was made as stated in Example 1. To a flask were added the crosslinked poly (allylamine) (12.5 grams; 6% crosslinked; ground to less than 30 mesh), (3-bromopropyl) dodecyldimethylammonium bromide (17.5 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (1.14 grams of 50% solution) was added and the stirring continued at 65° C. for two hours. Two additional aliquots of aqueous sodium hydroxide (1.14 grams of 50% solution) were sequentially added and the stirring continued at 65° C. for an additional two hours for each aliquot. Aqueous sodium hydroxide (1.14 grams of 50% solution) was then added and the stirring continued at 65° C. for an additional twelve hours. The mixture was then allowed to cool to room temperature.

The solid product was filtered off and washed by suspension, stirring for thirty minutes, and filtration, from the following fluids:

1. 459 mL 2 M NaCl (aqueous)
2. 459 mL 2 M NaCl (aqueous)
3. 2 L deionized water
4. 2 L deionized water
5. 2 L deionized water
6. 2 L deionized water The solid was then dried in a 60° C. forced-air oven to yield 17.4 grams of an off-white solid. The solid was then ground and passed through an 80 mesh sieve.

EXAMPLE 3

Alkylation of Crosslinked Poly(allylamine) with (3-bromopropyl)dodecyldimethylammonium bromide Crosslinked poly(allylamine) was made as stated in Example 1. To a flask were added the crosslinked poly (allylamine) (12.5 grams; 6% crosslinked; ground to less than 30 mesh), (3-bromopropyl) dodecyldimethylammonium bromide (35 grams; made by reaction of 1,3-dibromopropane and N,N-dimethyl-1-aminododecane in diethyl ether) and methanol (334 mL). The mixture was heated to 65° C. with stirring. Upon reaching 65° C., aqueous sodium hydroxide (1.99 grams of 50% solution) was added and the stirring continued at 65° C. for two hours. Two additional aliquots of aqueous sodium hydroxide (1.99 grams of 50% solution) were sequentially added and the stirring continued at 65° C. for an additional two hours for each aliquot. Aqueous sodium hydroxide (1.99 grams of 50% solution) was then added and the stirring continued at 65° C. for an additional twelve hours. The mixture was then allowed to cool to room temperature.

The solid product was filtered off and washed by suspension, stirring for thirty minutes, and filtration, from the following fluids 1. 459 mL 2 M NaCl (aqueous)
2. 459 mL 2 M NaCl (aqueous)
3. 2 L deionized water
4. 2 L deionized water
5. 2 L deionized water
6. 2 L deionized water The solid was then dried in a 60° C. forced-air drying oven to yield 25.6 grams of an off-white solid. The solid was ground and passed through an 80 mesh sieve.

EXAMPLE 4

Alkylation of Crosslinked Poly(allylamine) with (3-bromopropyl)dodecyldimethylammonium bromide Crosslinked poly(allylamine) was produced by the method of Example 1, with the exception that 16.7 mL of epichlorohydrin was employed, rather than 50 mL. To a flask were added crosslinked poly(allylamine) (12.5 grams; 2% crosslinked; ground to less than 30 mesh), (3-bromopropyl) dodecyldimethylammonium bromide (140.8 grams; made by reaction of 1,3-dibromopropane and N,N-dimethyl-1-aminododecane in diethyl ether), and methanol (334 mL). The mixture was heated to 65° C. with stirring Upon reaching 65° C., aqueous sodium hydroxide (7.1 grams of 50% solution) was added and the stirring continued at 65° C. for 2 hours. Two additional aliquots of aqueous sodium hydroxide (7.1 grams of 50% solution) were sequentially added and the stirring continued at 65° C. for an additional 2 hours for each aliquot. Aqueous sodium hydroxide (7.1 grams of 50% solution) was added and the stirring continued at 65° C. for an additional 12 hours. The mixture was then allowed to cool to room temperature.

The solid product was filtered off and washed by suspension, stirring for thirty minutes, and filtration from the following fluids:

1. 1.7 L 2 M NaCl (aqueous)
2. 1.7 L 2 M NaCl (aqueous)
3. 8 L deionized water
4. 8 L deionized water
5. 8 L deionized water
6. 8 L deionized water
7. 4 L deionized water The solid was then dried in a 60° C. forced-air drying oven to yield 39.8 grams of an off-white solid. The solid was ground and passed through an 80 mesh sieve.

EXAMPLE 5

Alkylation of Crosslinked Poly(allylamine) with (3-bromopropyl octyldimethylammonium bromide Crosslinked poly(allylamine) was made as stated in Example 1. To a flask were added crosslinked poly (allylamine) (12.5 grams; 6% crosslinked; ground to less than 30 mesh), (3-bromopropyl)octyldimethylammonium bromide (30.2 grams; made by reaction of 1,3-dibromopropane and N,N-dimethyl-1-aminooctane in diethyl ether), and methanol (334 mL). The mixture was heated to 65° C. with stirring Upon reaching 65° C. aqueous sodium hydroxide (2.0 grams of 50% solution) was added and the stirring continued at 65° C. for 2 hours. Two additional aliquots of aqueous sodium hydroxide (2.0 grams of 50% solution) were sequentially added and the stirring continued at 65° C. for an additional two hours for each aliquot. Aqueous sodium hydroxide (2.0 grams of 50% solution) was then added and the stirring continued at 65° C. for an additional twelve hours. The mixture was then allowed to cool to room temperature.

The solid product was filtered off and washed by suspension, stirring for thirty minutes, and filtration from the following fluids:

1. 800 mL 2 M NaCl (aqueous)
2. 800 mL 2 M NaCl (aqueous)
3. 2 L deionized water
4. 2 L deionized water
5. 1 L deionized water The solid was then dried in a 60° C. forced-air drying oven to yield 16.8 grams of an off-white solid. The solid was ground and passed through an 80 mesh sieve.

EXAMPLE 6

Alkylation of Crosslinked Poly(allylamine) with (6-bromohexyl)octyldimethylammonium bromide Crosslinked poly(allylamine) was made as stated in Example 1. To a flask were added crosslinked poly (allylamine) (12.5 grams; 6% crosslinked; ground to less than 30 mesh), (6-bromohexyl)octyldimethylaxmonium bromide (33.7 grams; made by reaction of 1,6-dibromohexane and N,N-dimethyl-1-aminooctane in diethyl ether), and methanol (334 mL). The mixture was heated to 65° C. with stirring. Upon reaching 65° C., aqueous sodium hydroxide (1.68 grams of 50% solution) was added and the stirring continued at 65° C. for two hours. Two additional aliquots of aqueous sodium hydroxide (1.68 grams of 50% solution) were sequentially added and the stirring continued at 65° C. for an additional two hours for each aliquot. Aqueous sodium hydroxide (1.68 grams of 50% solution) was added and the stirring continued at 65° C. for an additional twelve hours. The mixture was then allowed to cool to room temperature.

The solid product was filtered off and washed by suspensions stirring for thirty minutes, and filtration from the following fluids, 1. 1 L 2 H NaCl (aqueous)
2. 1 L 2 H NaCl (aqueous)
3. 1 L deionized water repeated until solution conductivity is less than 1 mS/cm The solid was then dried in a 60° C. forced air drying oven to yield 15.7 grams of an off-white solid. The solid was ground and passed through an 80 mesh sieve.

EXAMPLE 7

Alkylation of Crosslinked Poly(allylamine) with (4-bromobutyl dioctylmethylammonium bromide Crosslinked poly(allylamine) was made as stated in Example 1, with the exception that 25 mL of epichlorohydrin crosslinking agent was employed rather than 50 mL. To a flask were added the crosslinked poly(allylamine) (12.5 grams; 3% crosslinked; ground to less than 30 mesh), (4-bromobutyl)dioctylmethylammonium bromide (65.8 grams (crude); made by reaction of 1,4-dibromobutane and N,N-dioctylmethylamine in methanol), and methanol (334 mL). The mixture was heated to 65° C. with stirring Upon reaching 65° C., aqueous sodium hydroxide (3.28 grams of 50% solution) was added and the stirring continued at 65° C. for two hours. Two additional aliquots of aqueous sodium hydroxide (3.28 grams of 50% solution) were sequentially added and the stirring continued at 65° C. for an additional two hours for each aliquot. Aqueous sodium hydroxide (3.28 grams of 50% solution) was then added and the stirring continued at 65° C. for an additional twelve hours. The mixture was then allowed to cool to room temperature.

The solid product was filtered off and washed by suspension, stirring for thirty minutes, and filtration, from the following fluids:

1. 800 mL methanol
2. 1000 mL methanol
3. 890 mL 2 M NaCl (aqueous)
4. 890 mL 2 M NaCl (aqueous)
5. 2 L deionized water
6. 2 L deionized water The solid was then dried in a 60° C. forced-air oven to yield 27.1 grams of an off-white solid. The solid was then ground and passed through an 80 mesh sieve.

EXAMPLE 8

Preparation of (3-chloropropyl) dodecyldiethylammonium bromide

A two-liter, 3-necked, round-bottomed flask equipped with an air condenser and a magnetic stirring plate was charged with N,N-dimethyldodecylamine (297.24 grams, 1.40 moles), 1-bromo-3-chloropropane (220.44 grams, 1.40 moles) and methanol (250 mL). Reaction was maintained at 65 ° C. for 24 hours. Methanol was removed by rotary evaporation under reduced pressure to yield a brown sludge. To the sludge was added methyl-tert-butylether (2 liters)

causing a white solid to form The mixture was stirred for two hours and a semi-crystalline, white particulate was collected by vacuum filtration. The particulate was dried in a vacuum oven at 35° C. for 24 hours. Yield 228.2 grams (0.61 moles, 44%).

EXAMPLE 9

Alkylation of Crosslinked Poly(allylamine) with (3-chloropropyl)dodecyldimethylammonium bromide Crosslinked poly(allylamine) was made as stated in Example 1, with the exception that final crosslinking was 3 mole %. To a 2L, 3-necked flask equipped with a thermometer and a condenser were added crosslinked poly (allylamine) (25 grams; 3% crosslinked; ground to −10 mesh), (3-chloropropyl)dodecyldimethylammonium bromide (280 g=0.755 moles; prepared as stated in Example 8) and water (750 mL). The mixture was heated to 100° C. with stirring. Upon reaching 100° C., aqueous sodium hydroxide (6.1 grams of 50% solution) was added 10 times at equally spaced time points over the next 8 h. Stirring was continued at 100° C. for an additional sixteen hours. The mixture was then allowed to cool to room temperature.

Concentrated hydrochloric acid (50 mL) was added, the mixture stirred for 10 minutes, and the solid collected by filtration. The solid was rinsed on the funnel with 1.5 L of methanol. The solid product was filtered off and washed by suspension, stirring for thirty minutes, and filtration from the following fluids:

1. 1 L methanol
2. 3.3 L 2 M NaCl (aqueous)
3. 3.3 L 2 M NaCl (aqueous)
4. 3.3 L 2 M NaCl (aqueous)
5. 8 L deionized water The solid was then resuspended in deionized water (4 L) and the pH adjusted to 2.2 with HCl The solid was again collected by filtration (178.6 g) and then dried in a 60° C. forced-air oven to yield 111 g. The solid was then ground and passed through an 80 mesh sieve.

EXAMPLE 10

Alkylation of Crosslinked Poly(allylamine) with (3-chloro) propyl-dimethylhexylammonium bromide Example 9 was repeated, using (3-chloro)propyl-dimethylhexylammonium bromide (216.4 g) in place of 3-chloropropyldodecyldimethylammonium bromide. The yield was 85.6 g.

EXAMPLE 11

Alkylation of Crosslinked Poly(allylamine) with (3-chloropropyl)dimethylcyclohexylammonium bromide Example 9 was repeated, using (3-chloropropyl)-dimethylcyclohexylammonium bromide (213.2g)in place of (3-chloropropyl)dodecyldimethylammonium bromide. The yield was 86.4 g.

EXAMPLE 12

Alkylation of Crosslinked Poly(allylamine) with (3-chloropropyl)dimethyloctylammonium bromide Example 9 was repeated, using (3-chloropropyl)-dimethyloctylammonium bromide (237.7 g) in place of (3-chloropropyl)dodecyldimethylammonium bromide. The yield was 104.6 g.

EXAMPLE 13

Alkylation of Crosslinked Poly(allylamine) with (3-chloropropyl)dimethyldecylammonium bromide Example 9 was repeated using (3-chloropropyl)-dimethyldecylammonium bromide (269.4g) in place of (3-chloropropyl)dodecyldimethylammonium bromide. The yield was 101.7 g.

EXAMPLE 14

Alkylation of Crosslinked Poly(allylamine) with (3-chloropropyl)dimethyltetradecylammonium bromide Example 9 was repeated, using (3-chloropropyl)-dimethyltetradecylammonium bromide (301.2g) in place of (3-chloropropyl)dodecyldimethylammonium bromide. The yield was 112.3 g.

EXAMPLE 15

Alkylation of Crosslinked Poly(allylamine) with (3-chloropropyl)methyldioctylammonium bromide Example 9 was repeated, using (3-chloropropyl)-methyldioctylammonium bromide (272g) in place of (3-chloropropyl)dodecyldimethylammonium bromide and using 5.5 g of aqueous NaOH in each addition. The yield was 96.8 g.

EXAMPLE 16

Alkylation of Crosslinked Poly(allylamine) with (4-chlorobutyl methyldioctylammonium bromide Example 9 was repeated, using (4-chlorobutyl)-methyldioctylammonium bromide (241.6 g) in place of (3-chloropropyl)dodecyldimethylammonium bromide and using 4.4 g of aqueous NaOH in each additions The yield was 80.0 g.

EXAMPLE 17

Alkylation of Crosslinked Poly(allylamine) with (4-chlorobutyl)dimethyldodecylammonium bromide Example 9 was repeated, using (4-chlorobutyl)-dimethyldodecylammonium bromide (290.5 g) in place of (3-chloropropyl)dodecyldimethylammonium bromide The yield was 93.9 g.

EXAMPLE 18

Alkylation of Crosslinked Poly(allylamine) with (5-chloropentyl)methyldodecylammonium bromide Example 9 was repeated, using (5-chloropentyl)-methyldodecylammonium bromide (150.6 g) in place of (3-chloropropyl)dodecyldimethylammonium bromide and using 3.0 g of aqueous NaOH in each addition. The yield was 46.2 g.

EXAMPLE 19

Alkylation of Crosslinked Poly(allylamine) with (10-bromodecyl)trimethylammonium bromide Example 9 was repeated, using (10-bromodecyl) trimethylammonium bromide (271 0 g) in place of (3-chloro-propyl)dodecyldimethylammonium bromide. Water was added after 4 h (100 mL) and again after 8 h (100 mL). The yield was 101.8 g.

EXAMPLE 20

Alkylation of Crosslinked Poly(allylamine) with (6-chlorohexyl)dimethyldecylammonium bromide Example 9 was repeated, using (6-chlorohexyl) dimethyldecylammonium bromide (145.2g) in place of (3-chloropropyl)dodecyldimethylammonium bromide and using 3.0 g of aqueous NaOH in each addition. The yield was 46.2 g.

EXAMPLE 21

Preparation of (4-chlorobutyl) dimethyldodecylammonium bromide

Into a 1000 mL, round-bottomed flask equipped with air condensers and a magnetic stirring plate was charged N,N-dimethyldodecylamine (308.8 grams, 1.45 moles), 1-bromo-4-chlorobutane (249.98 grams, 1.45 moles) and 300 mL of methanol. The reaction was maintained at 65° C. for 48 hours. Solvent was removed by rotary evaporation under reduced pressure to yield brown oil. To the oil was added 100 ml of 1-butanol. The mixture was distilled under vacuum at 30° C. to 50° C. until distillate stopped collecting Yield 384.47 grams (0.99 moles, 69%).

EXAMPLE 22

Preparation of (2-chloroethyl) dimethyldodecylammonium bromide

Into a 1000 mL, round-bottomed flask equipped with air condensers and a magnetic stirring plate was charged N,N-dimethyldodecylamine (186.46 grams, 0.875 moles), 1-bromo-2-chloroethane (125.60 grams, 0.875 moles) and methanol (150 mL). The reaction was maintained at 65° C. for 48 hours. Solvent was removed by rotary evaporation under reduced pressure to yield brown oil. The oil was placed in a beaker and stirred with t-butylmethylether (2 L) causing a brownish white precipitate to form. The solids were collected by vacuum filtration. Solids were dried in a vacuum oven at 30° C. overnight Yield 197.0 grams (0.55 moles, 63%).

EXAMPLE 23

Comparison of Reactivity for Quaternary Ammonium Alkylating Agents

The alkylating agents (4-chlorobutyl) dodecyldimethylammonium bromide, (3-chloropropyl) dodecyldimethylammonium-bromide, and (2-chloroethyl) dodecyldimethylammonium bromide were prepared as stated in Examples 21, 8 and 22 respectively. Each alkylating agent was reacted under identical conditions with crosslinked poly(allylamine) as set forth in the procedure of Example 9. The reactivity of each alkylating agent with the amine of the poly(allyl-amine) backbone was assessed and compared.

The following results were obtained:

| Alkylating Agent | Starting Polymer | Alkylated Polymer | % Alkylation |
| --- | --- | --- | --- |
| (4-chlorobutyl)dodecyl-dimethylammonium bromide n = 4 | 25 g | 94 g | 109% |
| (3-chlorobutyl)dodecyl-dimethylammonium bromide n = 3 | 25 g | 111 g | 124% |
| (2-chloroethyl)dodecyl-dimethylammonium bromide n = 2 | 25 g | 28 g | 15% |

The percent alkylation is obtained using elemental analysis Single alkylation of each amine would correspond to 100% alkylation; double alkylation of each amine would correspond to 200% alkylation; triple alkylation of each amine would correspond to 300% alkylation. From the elemental analysis the N/C ratio for the polymer is obtained. Since the alkylating agent has a different N/C ratio than the base polymer, it is straightforward to determine how much of the given alkylating agent must have become attached to the polymer to change the N/C ratio from that obtained for the starting material to that obtained for the final product The result is expressed as the percent of the total amines in the polymer that have become alkylated, with numbers greater than 100 percent representing multiple alkylations on a single amine For example, the N/C ratio obtained for the starting material was 0.313. After alkylation with the n=3 alkylating agent, the N/C ratio has become 0.0922, which represents 124% alkylation. This calculation is performed using the equation:

$$\% \text{ Alkylated } (3.2*(N/C)-1)/(1-N/C*17)$$

where 3.2 is the C/N ratio for the starting material, and 17 is the C/N ratio for the alkylating agent (16 is used in the case of the n=2 alkylating agent, and 18 is used in the case of n=4).

From these results it is clear that the n=2 alkylating agent is much less effective in alkylating the amines of the amine polymer than the n=3 and n=4 agents We hypothesize that this effect is due to the influence of the quaternary amine on the reactivity of the alkyl halide group. Therefore, it can be concluded that the use of alkylating agents, wherein the quaternary amine is greater than 2 carbon atoms removed from carbon atom bearing the halogen of the alkyl halide, leads to unexpectedly improved reactivity over those alkylating agents with 2 carbon atoms or less.

EXAMPLE 24

Preparation of (3-chloropropyl) cyclohexyldimethylammonium bromide

A one-liter, 3-necked, Morton flask equipped with an air condenser and a magnetic stirring plate was charged with N,N-dimethylcyclohexylamine (210.06 grams, 1.65 moles), 1-bromo-3-chloropropane (259.99 grams, 1.65 moles) and methanol (250 mL). Reaction was maintained at 65° C. for 24 hours. Methanol was removed by rotary evaporation under reduced pressure to yield a brown sludge. To the sludge was added tert-butylmethylether (600 ml) causing an oil to form. The liquid phase was decanted from the oil and a second portion of methyl-tert-butylether (600 ml) was added. The mixture was stirred and liquid phase was decanted off from a thick sludge. To the sludge was added diethylether (600 mL) causing a white, semi-solid layer to form. The mixture was stirred and a liquid phase was removed. A white solid was placed in a vacuum oven at 35° C. for 24 hours. Yield 404.9 grams (1.42 molest 85%)

EXAMPLE 25

Preparation of (3-chloropropyl) tetradecyldimethylammonium bromide

A one-liter, 3-necked, round-bottomed flask equipped with air condensers and a magnetic stirring plate was charged with N,N-dimethyltetradecylamine (311.59 grams, 1.29 moles), 1-bromo-3-chloropropane (203.09 grams, 1.29 moles) and methanol (250 mL). Reaction was maintained at 65° C. for 24 hours. Methanol was removed by rotary evaporation under reduced pressure to yield a sludge. To the sludge was added methyl-tert-butylether (500 mL) causing a white solid to slowly form The mixture was stirred for one-half hour and white, paste-like particulate was collected by vacuum filtration. The solid was placed in a vacuum oven at 35° C. for 24 hours. Yield 420 grams (1.05 molest 82%).

EXAMPLE 26

Preparation of (3-chloropropyl) hexyldimethylammonium bromide

A 500 mL, 3-necked, round-bottomed flask equipped with air condensers and a magnetic stirring plate was charged with N,N-dimethylhexylamine (199.46 grams, 1.54 moles), 1-bromo-3-chloropropane (243.00 grams, 1.54 moles) and 250 mL of methanol The reaction was maintained at 65° C. for 24 hours. Solvent was removed by rotary evaporation under reduced pressure to yield a brown, viscous oil. Yield 445.8 grams (1.55 moles, 100%).

EXAMPLE 27

Preparation of (3-chloropropyl) odyldimethylammonium bromide

A 500 mL, 3-necked, round-bottomed flask equipped with air condensers and a magnetic stirring plate was charged with N,N-dimethyloctylamine (110.02 grams, 0.70 moles), 1-bromo-3-chloropropane (110.20 grams, 0.70 moles) and methanol (150 mL). The reaction was maintained at 65° C. for 24 hours. The solvent was removed by rotary evaporation under reduced pressure to yield a brown oil. The oil was extracted with methyl-tert-butylether (600 mL) by mixing together in a large breaker and decanting off excess solvent. This step was repeated 3 times. Additionally, the oil was extracted with diethylether (600 mL) and excess solvent was decanted. The viscous oil was dried in a vacuum oven at 35° C. overnight. Yield 174.14 grams (0.55 moles, 79%).

EXAMPLE 28

Preparation of (3-chloropropyl) octadecyldimethylammonium bromide

A 1000 mL, round-bottomed flask equipped with air condensers and a magnetic stirring plate was charged with N,N-dimethyloctadecylamine (301.0 grams, 1.01 moles), 1-bromo-3-chloropropane (1700 grams, 1.08 moles) and methanol (200 mL). The reaction was maintained at 65° C. for 18 hours. Solvent was removed by rotary evaporation under reduced pressure to yield clear oil. The oil was transferred to a beaker containing methylethylketone (250 mL) causing a white precipitate to form. Solid material was collected by vacuum filtration, resuspended in methylethylketone (250 mL) and collected by vacuum filtration an additional two times. The solid was placed in a vacuum oven at 30° C. overnight. Yield 274.9 grams (0.59 moles, 58%).

EXAMPLE 29

Preparation of (3-chloropropyl) decyldimethylammonium bromide

Into a 1000 mL, round-bottomed flask equipped with air condensers and a magnetic stirring plate was charged N,N-dimethyldecylamine (200.0 grams, 1.08 moles), 1-bromo-3-chloropropane (170 grams, 1.08 moles) and methanol (200 mL). The reaction was maintained at 65° C. for 18 hours. Solvent was removed by rotary evaporation under reduced pressure and furthermore with high vacuum distillation to yield brown oil. The oil was placed in a beaker and stirred with hexane/t-butylmethylether 1:1 solution (400 mL) causing a white precipitate The solids were collected by vacuum filtration. Solids were dried in a vacuum oven at 30° C. overnight. Yield 305.0 grams (0.089 moles, 82%).

EXAMPLE 30

Preparation of (3-chloropropyl) dioctylmethylammonium bromide

A one-liter, 3-necked, round-bottomed flask equipped with air condensers and a magnetic stirring plate was charged with N,N-dioctylmethylamine (202.48 grams, 0.79 moles), 1-bromo-3-chloropropane (124.8 grams, 0.79 moles) and methanol (250 mL). Reaction was maintained at 65° C. for two days. Methanol was removed by rotary evaporation under reduced pressure to yield an oil. To the oil was added ethylmethylketone (50 mL) and hexane (200 mL) causing a white solid to slowly form. The solvent was decanted from the mixture. The remaining solid was washed with hexane (50 mL) two times. The solid was placed in a vacuum oven at 35° C. for 24 hours. Yield 259 grams of a waxy solid (0.625 moles, 79%).

EXAMPLE 31

Preparation of (3-chloropropyl) didecylmethylammonium bromide

A two-liter, 3-necked, round-bottomed flask equipped with air condensers and a magnetic stirring plate was charged with N,N-didecylmethylamine (65.49 grams, 0.21 moles), 1-bromo-3-chloropropane (33.06 grams, 0.21 moles) and methanol (250 mL). Reaction was maintained at 65° C. for six days. Methanol was removed by rotary evaporation under reduced pressure to yield an oil. To the oil was added hexane (200 mL) causing a white solid to slowly form. The solvent was decanted off from the mixture. The remaining solid dried overnight under vacuum. Yield 81.67 grams 0.17 moles, 82%).

EXAMPLE 32

Preparation of (b-chlorohexyl) dodecyldimethylammonium bromide

To a 500 mL, round-bottomed flask equipped with air condensers and magnetic stirring was charged N,N-dimethyldodecylamine (95.13 grams, 0.513 moles), 1-bromo-6-chlorohexane (102.40 grams, 0.513 moles) and tert-butylmethylether (200 mL). The reaction was maintained at 58° C. for 14 hours. During this time a white precipitate formed. The reaction was cooled to room temperature and tert-butylmethylether (350 mL) was added. Solids were collected by vacuum filtration The mother liquor was allowed to react further at 60° C. and solids were collected in a similar fashion. The combined solids were dried in a vacuum oven at 35° C. for 24 hours, yielding 127.36 grams.

EXAMPLE 33

Preparation of (4-chlorobutyl) dioctylmethylammonium bromide

To a 500 mL, round-bottomed flask equipped with air condensers and magnetic stirring was charged N-methyldioctylamine (201.83 grams, 0.790 moles), 1-bromo-4-chlorobutane (135.517 grams, 0.790 moles) and methanol (250 mL). The reaction was maintained at 68° C. for 48 hours. The reaction was cooled to room temperature. Solvent was removed by rotary evaporation until a thick oil remained. Solvent removal was continued under high vacuum at 50° C., yielding 333.53 grams of a thick brown oil.

EXAMPLE 34

Preparation of (5-chloropentyl) dodecyldimethylammonium bromide

To a 500 mL, round-bottomed flask equipped with air condensers and magnetic stirring was charged N,N-dimethyldododecylamine (230.17 grams, 1.078 moles), 1-bromo-5-chloropentane (199.77 grams, 1.076 moles) and tert-butylmethylether (250 mL). After two hours of heating at 60° C. the reaction becomes thick and white with precipitate Additional tert-butylmethylether (250 mL) was added. The reaction was maintained at 60° C. for 24 hours. The reaction was cooled to room temperature and the solids were collected by vacuum filtration. Solids were dried in a vacuum oven at 35° C. for 24 hours, yielding 207.40 grams.

EXAMPLE 35

Preparation of Crosslinked Poly(vinylamine); Alkylation of Crosslinked Poly(vinylamine) with (3-chloropropyl)dimethyldodecylammonium bromide Poly(vinylamine) free base (mw=40,000; Air Products; 62.5 g) was dissolved in water (188 mL) and methanol (250 mL). Epichlorohydrin (2.8 g) was added and the mixture stirred until it gelled. The gel was broken up and suspended in water (13 L). The solid was collected by filtration and dried in a forced air oven at 60° C. to yield 75.2g of solid. This solid was ground and passed through a 10 mesh sieve.

The ground solid (14.8 g) was reacted in a manner similar to Example 9, using 140 g of (3-chloropropyl)-dimethyldodecylammonium bromide and 30 g of aqueous base, yielding 57.7 g of product Efficacy Comparison of Examples 10, 12, 13, and 19

Examples 10, 12, 13, and 19 are made from the alkylating agents of the form:

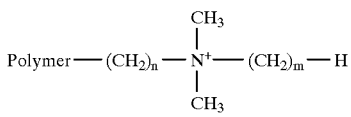

where we have the following:

| Example | n | m | Longest Hydrophobe | Total Carbons |
|---|---|---|---|---|
| 10 | 3 | 6 | 6 | 11 |
| 12 | 3 | 8 | 8 | 13 |
| 13 | 3 | 10 | 10 | 15 |
| 19 | 10 | 1 | 10 | 13 |

Examples 10, 12 and 13 are examples of the present invention, which include a terminal hydrophobic alkyl group The hydrophobic alkyl group has a chain length of 6 in Example 10, 8 in Example 12, and 10 in Example 13. The hydrocarbon chain (n=10) in Example 19 is not considered to be a terminal hydrophobic group as it is attached to the quaternary amine at one end and the amine of the polymer backbone at the other end.

These examples are believed to be appropriate comparisons of the differences between the efficacy resulting from free, or terminal, hydrophobe groups, and those that are internal to the alkylating agent, between the quaternary amine and the amine polymer. Compared to Example 19 (an example of the hydrophobe between the quaternary amine and the amine polymer), these examples were selected to have either the same total number of carbon atoms (Example 12), or the same single hydrophobe length (Example 13), or the same number of carbons in one unbranched segment (11; Example 10). Further, based on the yields of the alkylation reactions, these polymers all have a similar number of alkylating agents attached to the polymer backbone.

The sequestrants made in Examples 10, 12, 13 and 19 were tested in vivo in hamsters. The animals injected peritoneally with a solution of $^{14}C$ labeled bile acids (Cholic and Chenodeoxycholic acids). The labeled bile acids are presented in the same ratio (3:1; Cholic:Cheno) that they exist in gall bladder bile. They enter the gall bladder and are incorporated into the animals's endogenous pool. The animals are then fed diet containing drug for 36 hours while the feces are collected over the final 29 hours. Fecal samples are processed and counted for radioactivity Results are expressed as percent or radio label excreted over control animals that were not fed as sequestrant.

| Example | Activity* |
|---|---|
| 10 | 184% |
| 12 | 200% |
| 13 | 184% |
| 19 | 143% |

*Radioactivity excreted per gram of feces compared to no-sequestrant control.

From these data it is evident that for sequestrants with equivalent "hydrophobe" chain lengths, that the terminal hydrophobic alkyl groups result in significantly more potent sequestrants than those wherein the hydrophobic alkyl group is internal.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A crosslinked poly(allylamine) polymer, comprising a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having between one and about five carbons.

2. The crosslinked poly(allylamine) polymer of claim 1, wherein said alkylene has three carbons, the hydrophobic alkyl group is an octyl group and the remaining terminal substituents are methyl groups.

3. The crosslinked poly(allylamine) polymer of claim 1, wherein said alkylene has three carbons, the hydrophobic alkyl group is a decyl group and the remaining terminal substituents are methyl groups.

4. The crosslinked poly(allylamine) polymer of claim 1, wherein said alkylene has three carbons, the hydrophobic alkyl group is a dodecyl group and the remaining terminal substituents are methyl groups.

5. The crosslinked poly(allylamine) polymer of claim 1, wherein said alkylene has four carbons, the hydrophobic alkyl group is an octyl group and the remaining terminal substituents are methyl groups.

6. The crosslinked poly(allylamine) polymer of claim 1, wherein said alkylene has four carbons, the hydrophobic alkyl group is a decyl group and the remaining terminal substituents are methyl groups.

7. The crosslinked poly(allylamine) polymer of claim 1, wherein said alkylene has four carbons, the hydrophobic alkyl group is a dodecyl group and the remaining terminal substituents are methyl groups.

8. The crosslinked poly(allylamine) polymer of claim 1, wherein said alkylene has five carbons, the hydrophobic alkyl group is an octyl group and the remaining terminal substituents are methyl groups.

9. The crosslinked poly(allylamine) polymer of claim 1, wherein said alkylene has five carbons, the hydrophobic alkyl group is a decyl group and the remaining terminal substituents are methyl groups.

10. The crosslinked poly(allylamine) polymer of claim 1, wherein said alkylene has five carbons, the hydrophobic alkyl group is a dodecyl group and the remaining terminal substituents are methyl groups.

11. The crosslinked poly(allylamine) polymer of claim 1, wherein said alkylene has six carbons, the hydrophobic alkyl group is an octyl group and the remaining terminal substituents are methyl groups.

12. The crosslinked poly(allylamine) polymer of claim 1, wherein said alkylene has six carbons, the hydrophobic alkyl group is a decyl group and the remaining terminal substituents are methyl groups.

13. The crosslinked poly(allylamine) polymer of claim 1, wherein said alkylene has six carbons, the hydrophobic alkyl group is a dodecyl group and the remaining terminal substituents are methyl groups.

14. A crosslinked poly(allylamine) polymer formed by a method comprising the step of reacting a crosslinked poly(allylamine) with a quaternary amine-containing compound having the formula

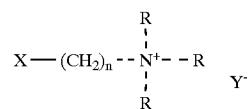

wherein,

R represents an alkyl group, at least one of which has from six to about twenty-four carbons and the remainder of which each independently have from one to about five carbons, n is an integer having a value of three or more, X is a leaving group, and Y is a negatively-charged counterion.

15. The crosslinked poly(allylamine) polymer of claim 14, wherein n is from 3 to about 6.

16. The crosslinked poly(allylamine) polymer of claim 15, wherein n is 3, at least one alkyl is an octyl group and the remaining alkyl groups are methyl groups.

17. The crosslinked poly(allylamine) polymer of claim 15, wherein n is 3, at least one alkyl is a decyl group and the remaining alkyl groups are methyl groups.

18. The crosslinked poly(allylamine) polymer of claim 15, wherein n is 3, at least one alkyl group is a dodecyl group and the remaining alkyl groups are methyl groups.

19. The crosslinked poly(allylamine) polymer of claim 15, wherein n is 4, at least one alkyl group is an octyl group and the remaining alkyl groups are methyl groups.

20. The crosslinked poly(allylamine) polymer of claim 15, wherein n is 4, at least one alkyl group is a decyl group and the remaining alkyl groups are methyl groups.

21. The crosslinked poly(allylamine) polymer of claim 15, wherein n is 4, at least one alkyl group is a dodecyl group and the remaining alkyl groups are methyl groups.

22. The crosslinked poly(allylamine) polymer of claim 15, wherein n is 5, at least one alkyl group is an octyl group and the remaining alkyl groups are methyl groups.

23. The crosslinked poly(allylamine) polymer of claim 15, wherein n is 5, at least one alkyl group is a decyl group and the remaining alkyl groups are methyl groups.

24. The crosslinked poly(allylamine) polymer of claim 15, wherein n is 5, at least one alkyl group is a dodecyl group and the remaining alkyl groups are methyl. groups.

25. The crosslinked poly(allylamine) polymer of claim 15, wherein n is 6, at least one alkyl group is an octyl group and the remaining alkyl groups are methyl groups.

26. The crosslinked poly(allylamine) polymer of claim 15 wherein n is 6, at least one alkyl is a decyl group and the remaining alkyl groups are methyl groups.

27. The crosslinked poly(allylamine) polymer of claim 15, wherein n is 6, at least one alkyl group is a dodecyl group and the remaining alkyl groups are methyl groups.

28. A hydrocarbon amine polymer, comprising a substituent bound to an amine of said polymer, the substituent including a quaternary amine-containing moiety, wherein a quaternary amine nitrogen of said moiety is bound to the amine of the polymer by an alkylene having three or more carbons and wherein at least two of three terminal substituents of the quaternary amine are each a hydrophobic alkyl group having from six to about twenty-four carbons and the other terminal substituent is an alkyl group having from one to about five carbons.

29. The hydrocarbon amine polymer of claim 28, wherein the polymer is crosslinked.

30. A hydrocarbon amine polymer, comprising a substituent bound to an amine of said polymer, the substituent including a quaternary amine-containing moiety, wherein a quaternary amine nitrogen of said moiety is bound to the amine of the polymer by an alkylene having three or more carbons and wherein three terminal substituents of the quaternary amine are hydrophobic alkyl groups having from six to about twenty-four carbons.

31. The hydrocarbon amine polymer of claim 30, wherein the polymer is crosslinked.

32. A crosslinked hydrocarbon amine polymer formed by a method comprising the step of reacting a crosslinked hydrocarbon amine polymer with a quaternary amine-containing compound having the formula:

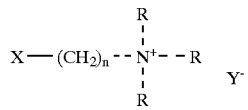

wherein,
R represents an alkyl group, at least one of which has from six to about twenty-four carbons, and the remainder of which each independently have from one to about five carbons,
n is an integer having a value of three or more,
X is a leaving group, and
Y is a negatively-charged counterion.

33. The crosslinked hydrocarbon amine polymer of claim 32, wherein the polymer is a poly(vinylamine) polymer.

34. The crosslinked hydrocarbon amine polymer of claim 32, wherein the polymer is a poly(allylamine) polymer.

35. The crosslinked hydrocarbon amine polymer of claim 32, wherein the polymer is a poly(ethylenimine) polymer.

36. A method for binding bile salts in a mammal, comprising the step of orally administering to the mammal a therapeutic amount of a crosslinked poly(allylamine) polymer having a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having from one to about five carbons.

37. A method for binding bile salts in a mammal, comprising the step of orally administering to the mammal a therapeutic amount of a hydrocarbon amine polymer having a substituent bound to an amine of said polymer, the substituent including a quaternary amine containing moiety, wherein a quaternary amine nitrogen of said moiety is bound to the amine of the polymer by an alkylene having three or more carbons and wherein at least two of three terminal substituents of the quaternary amine are hydrophobic alkyl groups having from six to about twenty-four carbons and the remaining terminal substituent is an alkyl group having from one to about five carbons.

38. A method for reducing blood cholesterol in a mammal, comprising the step of orally administering to the mammal a therapeutic amount of a crosslinked poly(allylamine) polymer having a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having from one to about five carbons.

39. A method for treating atherosclerosis in a mammal, comprising the step of orally administering to the mammal a therapeutic amount of a crosslinked poly(allylamine) polymer having a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having from one to about five carbons.

40. A method for treating hypercholesterolemia in a mammal, comprising the step of orally administering to the mammal a therapeutic amount of a crosslinked poly(allylamine) polymer having a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having between one and about five carbons.

41. A method for reducing plasma lipid content of a mammal, comprising the step of orally administering to the mammal a therapeutic amount of a crosslinked poly(allylamine) polymer having a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having between six and about twenty-four carbons and the remaining terminal substituents are each independently an alkyl group having from one to about five carbons.

42. A poly(allylamine) polymer, comprising a substituent bound to an amine of said polymer, the substituent including a quaternary amine-containing moiety, wherein a quaternary amine nitrogen of said moiety is bound to the amine of the polymer by an alkylene having three or more carbons and wherein at least one of three terminal substituents of the quaternary amine is a hydrophobic alkyl group having from six to about twenty-four carbons and the remaining terminal substituents are each independently an alkyl group having from one to about five carbons.

43. The poly(allylamine) polymer of claim 42, wherein said alkylene has three carbons, the hydrophobic alkyl group is an octyl group and the remaining terminal substituents are methyl groups.

44. The poly(allylamine) polymer of claim 42, wherein said alkylene has three carbons, the hydrophobic alkyl group is a decyl group and the remaining terminal substituents are methyl groups.

45. The poly(allylamine) polymer of claim 42, wherein said alkylene has three carbons, the hydrophobic alkyl group is a dodecyl group and the remaining terminal substituents are methyl groups.

46. The poly(allylamine) polymer of claim 42, wherein said alkylene has four carbons, the hydrophobic alkyl group is a octyl group and the remaining terminal substituents are methyl groups.

47. The poly(allylamine) polymer of claim 42, wherein said alkylene has four carbons, the hydrophobic alkyl group is a decyl group and the remaining terminal substituents are methyl groups.

48. The poly(allylamine) polymer of claim 42, wherein said alkylene has four carbons, the hydrophobic alkyl group is an dodecyl group and the remaining terminal substituents are methyl groups.

49. The poly(allylamine) polymer of claim 42, wherein said alkylene has five carbons, the hydrophobic alkyl group is an octyl group and the remaining terminal substituents are methyl groups.

50. The poly(allylamine) polymer of claim 42, wherein said alkylene has five carbons, the hydrophobic alkyl group is a decyl group and the remaining terminal substituents are methyl groups.

51. The poly(allylamine) polymer of claim 42, wherein said alkylene has five carbons, the hydrophobic alkyl group is a dodecyl group and the remaining terminal substituents are methyl groups.

52. The poly(allylamine) polymer of claim 42, wherein said alkylene has six carbons, the hydrophobic alkyl group is an octyl group and the remaining terminal substituents are methyl groups.

53. The poly(allylamine) polymer of claim 42, wherein said alkylene has six carbons, the hydrophobic alkyl group is a decyl group and the remaining terminal substituents are methyl groups.

54. The poly(allylamine) polymer of claim 42, wherein said alkylene has six carbons, the hydrophobic alkyl group is a dodecyl group and the remaining terminal substituents are methyl groups.

* * * * *